(12) United States Patent
Shortt et al.

(10) Patent No.: US 7,304,310 B1
(45) Date of Patent: Dec. 4, 2007

(54) METHODS AND SYSTEMS FOR INSPECTING A SPECIMEN USING LIGHT SCATTERED IN DIFFERENT WAVELENGTH RANGES

(75) Inventors: David Shortt, Milpitas, CA (US); Christian Wolters, Campbell, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 242 days.

(21) Appl. No.: 10/719,347

(22) Filed: Nov. 21, 2003

(51) Int. Cl.
*G01J 3/00* (2006.01)
(52) U.S. Cl. .................................................. 250/372
(58) Field of Classification Search ............ 356/243.7, 356/237.4, 237.5
See application file for complete search history.

(56) References Cited

U.S. PATENT DOCUMENTS

| | | | |
|---|---|---|---|
| 4,556,903 A | 12/1985 | Blitchington et al. | |
| 4,844,617 A | 7/1989 | Kelderman et al. | |
| 5,717,518 A | 2/1998 | Shafer et al. | |
| 5,771,094 A | 6/1998 | Carter et al. | |
| 5,936,726 A * | 8/1999 | Takeda et al. ............ | 356/237.2 |
| 5,956,174 A | 9/1999 | Shafer et al. | |
| 6,133,576 A | 10/2000 | Shafer et al. | |
| 6,201,601 B1 | 3/2001 | Vaez-Iravani et al. | |
| 6,271,916 B1 | 8/2001 | Marxer et al. | |
| 6,313,467 B1 | 11/2001 | Shafer et al. | |
| RE37,740 E | 6/2002 | Chadwick et al. | |
| 6,538,730 B2 * | 3/2003 | Vaez-Iravani et al. ... | 356/237.2 |
| 6,597,000 B2 | 7/2003 | Stern | |
| 6,618,134 B2 * | 9/2003 | Vaez-Iravani et al. ... | 356/237.4 |
| 6,657,714 B2 * | 12/2003 | Almogy et al. .......... | 356/237.3 |
| 6,914,670 B1 * | 7/2005 | Almogy et al. ............ | 356/236 |
| 2002/0054291 A1 * | 5/2002 | Tsai et al. ................... | 356/394 |
| 2002/0093648 A1 * | 7/2002 | Nikoonahad et al. ..... | 356/237.1 |
| 2002/0105636 A1 * | 8/2002 | Okawauchi ............... | 356/237.4 |
| 2002/0109110 A1 * | 8/2002 | Some et al. ............. | 250/559.4 |
| 2003/0058433 A1 * | 3/2003 | Almogy et al. .......... | 356/237.1 |
| 2005/0073686 A1 * | 4/2005 | Roth et al. ................... | 356/436 |

* cited by examiner

*Primary Examiner*—David Porta
*Assistant Examiner*—Djura Malevic
(74) *Attorney, Agent, or Firm*—Baker & McKenzie LLP (57) ABSTRACT

Methods and systems for inspecting a specimen are provided. One method includes directing ultraviolet light to a specimen. The method also includes detecting light scattered from the specimen having a selected wavelength range. In addition, the method includes detecting features, defects, or light scattering properties of the specimen using signals representative of the detected light. One inspection system includes an illumination subsystem configured to direct ultraviolet light to a specimen. The system also includes a channel configured to detect light scattered from the specimen having a selected wavelength range. In addition, the system includes a processor configured to detect features, defects, or light scattering properties of the specimen using signals that are representative of the detected light.

25 Claims, 3 Drawing Sheets

METHODS AND SYSTEMS FOR INSPECTING A SPECIMEN USING LIGHT SCATTERED IN DIFFERENT WAVELENGTH RANGES

BACKGROUND OF THE INVENTION

1. Field of the Invention

The present invention generally relates to methods and systems for inspecting a specimen using light scattered in different wavelength ranges. Certain embodiments relate to separately detecting scattered light having one or more wavelengths that are longer or shorter than an incident wavelength.

2. Description of the Related Art

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor fabrication process, defects such as particulate contamination and pattern defects may be introduced into semiconductor devices. Such defects may be found either randomly on a specimen surface or may be repeated within each device formed on a specimen. For example, random defects may be caused by events such as contamination in a manufacturing environment and contamination in process chemicals used in fabrication of a semiconductor device. Defects may also be formed in a systematic fashion over time and due to individual process marginalities and interactions of multiple processes. Defects caused by individual process marginalities or by interactions between multiple processes may result in defects such as a film thickness variation or a lateral dimension variation due to dose variation. Such defects may, in turn, result in a defect in a semiconductor device formed on the specimen such as bridging between two conductive structures thereby forming a short between the structures. Defects repeated within each semiconductor device formed on an entire specimen may, for example, be systematically caused by contamination or defects found on a reticle, or a mask. Contamination or defects on a reticle may be transferred along with a device pattern to a resist during a lithography process.

As the dimensions of advanced semiconductor devices continue to shrink, the presence of defects in the semiconductor devices limits the successful fabrication, or yield, of a semiconductor device. For example, a reticle defect reproduced in a resist patterned during lithography may cause an open circuit or a short circuit in a semiconductor device formed in subsequent processing. Because fabrication of a semiconductor device includes many complex process steps, the adverse effects of defects on total yield may increase exponentially if an error that is caused by a defect is propagated throughout an entire manufacturing process or operation over time.

SUMMARY OF THE INVENTION

One embodiment of the invention relates to a method for inspecting a specimen. The method includes directing ultraviolet light to the specimen. In some embodiments, the ultraviolet light includes nearly monochromatic ultraviolet light. The method also includes detecting light scattered from the specimen. The detected light has a selected wavelength range. The wavelength range may be selected such that light fluoresced from the specimen is not detected. In one embodiment, the wavelength range may include wavelengths within about 1 nm to about 10 nm of a wavelength of the ultraviolet light. Alternatively, the wavelength range may be selected such that the detected light includes light fluoresced from the specimen. In another alternative, the wavelength range may include wavelengths shorter than a wavelength of the ultraviolet light.

In some embodiments, detecting the scattered light may include detecting light scattered from the specimen with two channels. The two channels may be arranged at different collection angles. The two channels may include two or more detectors arranged at a first of the different collections angles and two or more detectors arranged at a second of the different collection angles. In addition, the light detected by the two channels may have different selected wavelength ranges. One of the different selected wavelength ranges may be selected such that the detected light has a wavelength that is approximately the same as a wavelength of the ultraviolet light. Another of the different selected wavelength ranges may be selected such that the detected light includes light fluoresced from the specimen.

In other embodiments, detecting the scattered light may include detecting the light scattered from the specimen with two channels, and the light detected by the two channels may have the same selected wavelength range. In one embodiment, the wavelength range of the two channels may be selected such that light fluoresced from the specimen is not detected. Alternatively, the wavelength range of the two channels may be selected such that the detected light includes light fluoresced from the specimen. The two channels may be arranged at different collection angles. In addition, the two channels may include one or more detectors arranged at the different collection angles.

In addition, the method includes detecting features, defects, or light scattering properties of the specimen using signals representative of the detected light. The method may further include classifying the features or defects using signals representative of the detected light. This embodiment may include additional steps described herein.

An additional embodiment relates to a method for inspecting a specimen. This method includes directing ultraviolet light to the specimen. The method also includes detecting light scattered from the specimen with one or more channels. Each of the one or more channels includes one or more detectors. In addition, each of the one or more detectors has an independently selected wavelength range. The method further includes detecting features, defects, or light scattering properties of the specimen using signals representative of the detected light. In some embodiments, the method may include classifying the features or defects using signals representative of the detected light. This embodiment may also include additional steps described herein.

Another embodiment relates to a method for inspecting a specimen that includes directing light having one or more incident wavelengths to a specimen. In one embodiment, the one or more incident wavelengths may be selected to stimulate fluorescence emission from one or more materials on the specimen. In some embodiments, the one or more incident wavelengths are ultraviolet wavelengths. The method also includes separately detecting a first portion and a second portion of light scattered from the specimen substantially simultaneously. In another embodiment, directing light to the specimen and detecting the scattered light may be performed in a non-confocal mode and/or a darkfield mode.

The first portion of the scattered light has a wavelength range selected such that the first portion does not include light fluoresced from the specimen. In one embodiment, the wavelength range of the first portion may include wavelengths within about 1 nm to about 10 nm of the one or more incident wavelengths. The second portion of the scattered light has a wavelength range selected such that the second portion includes light fluoresced from the specimen.

In some embodiments, the method may also include separately detecting a third portion of the light scattered from the specimen. In one such embodiment, a wavelength range of the third portion is selected to include wavelengths shorter than the one or more incident wavelengths. In a different embodiment, a wavelength range of the third portion is selected such that the third portion includes light fluoresced from the specimen at wavelengths different than those of the second portion.

In addition, the method includes detecting features, defects, or light scattering properties of the specimen using signals representative of the first and second portions of the light. In some embodiments, the method may further include classifying the features or the defects using an intensity of the first portion of the detected light, an intensity of the second portion of the detected light, or a combination thereof. The method may include additional steps described herein.

An additional embodiment relates to an inspection system. The system includes an illumination subsystem configured to direct ultraviolet light to a specimen. The system also includes a channel configured to detect light scattered from the specimen having a selected wavelength range. In one embodiment, the wavelength range is selected such that light fluoresced from the specimen is not detected. In a different embodiment, the wavelength range may be selected such that light fluoresced from the specimen is detected. In a further embodiment, the wavelength range may include wavelengths that are shorter than a wavelength of the ultraviolet light. The system may also include multiple channels as described herein. In one such embodiment, the different channels may be configured to detect light scattered from the specimen having independently selected wavelength ranges.

For example, the system may also include a second channel. The two channels may be arranged at different collection angles or at the same collection angle. In addition, the two channels may include different types of detectors or the same type of detectors. In one embodiment, the channel may include a bandpass filter, and the second channel may include an edge filter, a notch filter, or a combination thereof. In some embodiments, the channel may include one or more spectral filters, and the one or more spectral filters may be selected based on one or more materials of the specimen. In addition, the second channel may be configured to detect light scattered from the specimen having a second selected wavelength range. The second wavelength range may be selected to include wavelengths that are shorter than a wavelength of the ultraviolet light or longer than the wavelength of the ultraviolet light. The system may also include more than two detection channels. In another embodiment, the illumination subsystem and the channel(s) form a non-confocal and/or darkfield optical subsystem.

The system further includes a processor configured to detect features, defects, or light scattering properties of the specimen using signals that are representative of the detected light. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The methods and systems described herein enhance defect detection by collecting well-defined wavelength ranges of scattered light, specifically including ranges around the incident wavelength and/or ranges of wavelengths longer and/or shorter than the incident wavelength. In contrast, in some currently used inspection methods, scattered light is not distinguished by wavelength ranges other than the natural sensitivity of the detector(s). In addition, currently used inspection methods that include measuring light across the full available wavelength range of both features of interest and background features is not optimal since for many applications it results in relatively low signal-to-noise ratios.

In the methods and systems described herein, however, the detected wavelength range(s) in the scattered light spectrum are adjustable for each application. In one type of application such as an organic film subject to fluorescence effects, scattered light having wavelengths longer than the incident wavelength may contribute largely to what is considered the background signal representative of the surface while light scattered from features of interest (e.g., particle contamination) may fall in a wavelength range much closer to the incident wavelength. Therefore, narrowing the detected wavelength spectrum to a narrow range around the incidence wavelength improves the signal-to-noise ratio significantly. On the other hand, using the same fluorescence example, it might be true that the fluorescence of the surface itself is an important indicator of film properties, in which case it would be advantageous to specifically detect scattered wavelengths longer than the incident wavelength. In other applications, light scattered from the wafer surface may fall in a narrow wavelength range around the incident wavelength, while scattering from particles or other defects may contain a significant amount of light in a wavelength range longer than the wavelength of the incident light. In those cases, the signal-to-noise ratio is, improved by limiting the detectable wavelength spectrum to a range longer than the incidence wavelength.

At present, the inventors have seen direct evidence of fluorescence effects in some films, so it is known that wavelengths longer than the incident wavelength are important and detection of such wavelengths of scattered light are advantageous. However, there may also be unusual mechanisms (e.g., non-linear optical effects), which might make wavelengths shorter than the incident wavelength useful as well.

In addition to improved detection made possible by increased signal-to-noise ratios, using several detectors to detect light having different wavelength ranges allows discrimination and classification of defects and/or features of interest with different scattering spectra. For example, many types of organic materials (e.g., photoresist particles) that have a significant contribution from longer wavelength fluorescence in their scattering spectrum could be discriminated from inorganic material (e.g., metal particles) with no or low contributions of fluorescence in their scattering spectrum. Therefore, one main advantage of the systems and methods described herein is increased capture, discrimination, and classification of defects and/or features of interest in cases where wavelengths other than the incident wavelength make up a significant portion of the scattering spectrum.

The term "specimen" is used herein to refer to a wafer, a reticle, or any other sample that may be inspected for defects, features, or other information (e.g., an amount of haze or film properties) known in the art.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers that may be formed upon a substrate. For example, such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, other devices such as microelectromechanical (MEMS) devices and the like may also be formed on a wafer.

A "reticle" may be a reticle at any stage of a reticle fabrication process or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

Figure 1:
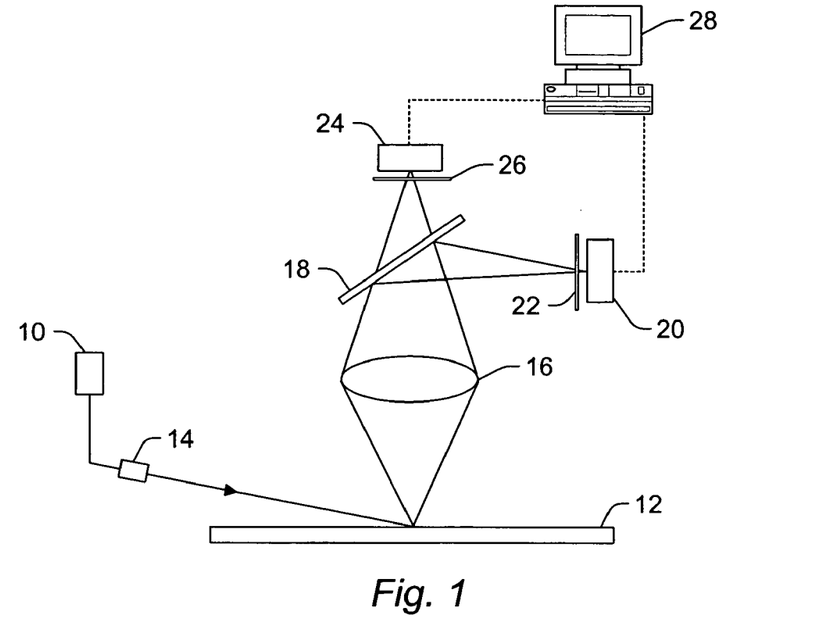
FIGS. 1-3 are schematic diagrams illustrating various inspection systems that can be used to inspect a specimen as described herein.
Figure 2:
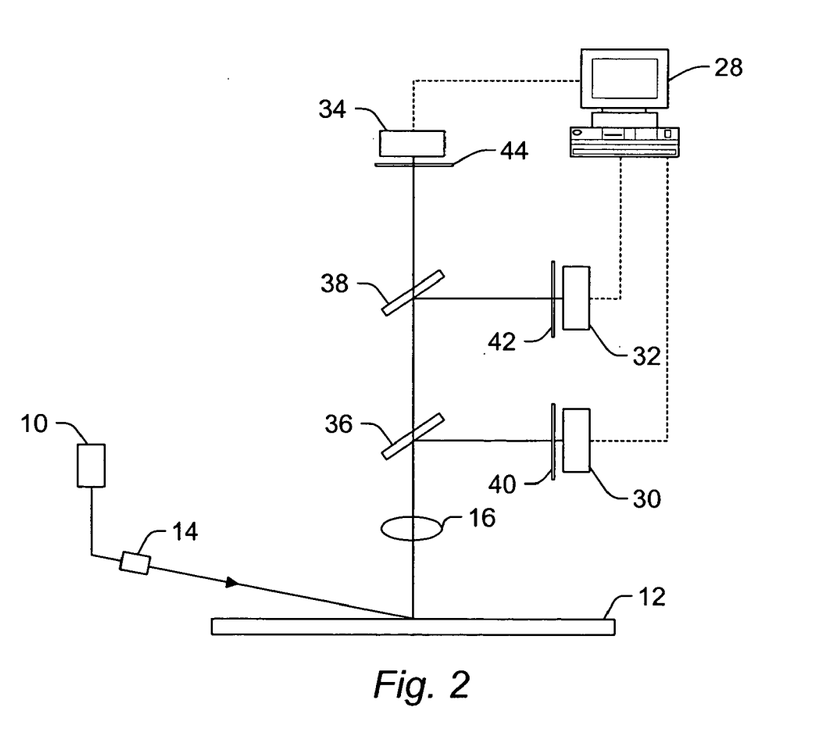
Figure 3:
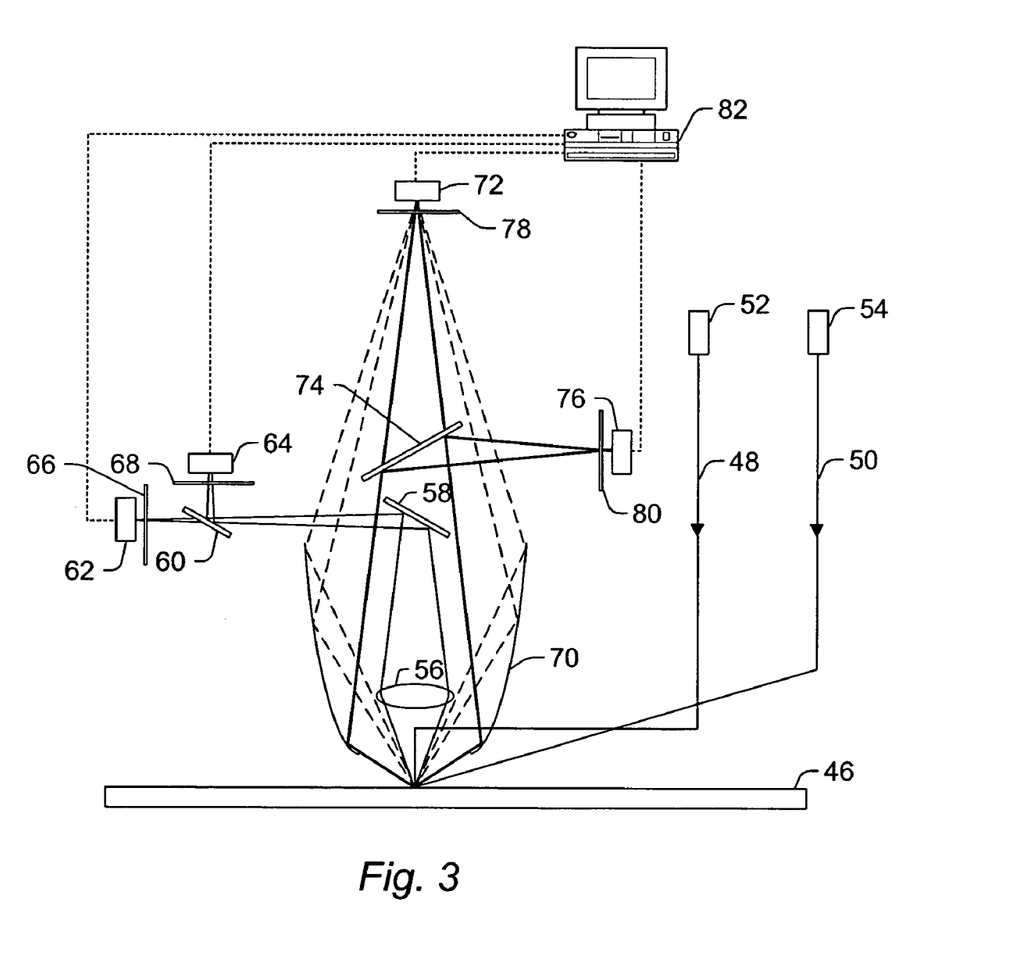

Turning now to the drawings, it is noted that FIGS. 1-3 are not drawn to scale. In particular, the scale of some of the elements of the figures are greatly exaggerated to emphasize characteristics of the elements. It is also noted that FIGS. 1-3 are not drawn to the same scale. Elements shown in more than one figure that may be similarly configured have been indicated using the same reference numerals.

FIG. 1 illustrates a system that may be used to perform the inspection methods described herein. The system shown in FIG. 1 illustrates a general optical configuration that can be used to inspect a specimen according to the methods described herein. The inspection system includes a non-confocal, darkfield optical subsystem. It will be obvious to one of ordinary skill in the art that the illustrated system may be altered in many ways while still providing the capability to perform the methods described herein. For example, the collection lens may be replaced by a reflective or partially reflective collector. In addition, it will be obvious to one of ordinary skill in the art that the illustrated system may include various additional components that are not shown in FIG. 1 such as a stage, a specimen handler, folding mirrors, polarizers, additional light sources, additional detectors, additional collectors, etc. All such variations are within the scope of the invention described herein.

The system illustrated in FIG. 1 includes an illumination subsystem. The illumination subsystem is configured to direct light having one or more incident wavelengths to a specimen. For example, the illumination subsystem includes light source 10. Light source 10 may include, for example, a laser, a diode laser, a helium neon laser, an argon laser, a solid state laser, a diode pumped solid state (DPSS) laser, a xenon arc lamp, a gas discharging lamp, or an incandescent lamp. The light source may be configured to emit near monochromatic light or broadband light. In general, the illumination subsystem is configured to direct light having a relatively narrow wavelength band to the specimen (e.g., nearly monochromatic light or light having a wavelength range of less than about 20 nm, less than about 10 nm, less than about 5 nm, or even less than about 2 nm). Therefore, if the light source is a broadband light source, the illumination subsystem may also include one or more spectral filters that may limit the wavelength of the light directed to the specimen. The one or more spectral filters may be bandpass filters and/or edge filters and/or notch filters.

The wavelengths of light that are directed to the specimen may vary depending on materials of the specimen. For example, the one or more incident wavelengths may be selected to stimulate fluorescence emission from one or more materials on the specimen. In some embodiments, the one or more incident wavelengths are ultraviolet wavelengths. In one embodiment, the incident ultraviolet light may have a wavelength of about 355 nm or about 364 nm. However, some visible wavelengths may also stimulate fluorescence emission from some materials. Examples of appropriate visible wavelengths include, but are not limited to, 442 nm and 488 nm.

The light source may be configured to emit light of various polarizations. In addition, the illumination subsystem may include one or more polarizing components that may alter the polarization characteristics of the light emitted by the light source. The light directed to specimen 12 may also be coherent or incoherent, but coherent monochromatic illumination may be preferred if the system is to filter out signals from pattern features or edge features using Fourier filtering as described herein. The illumination subsystem may also include a number of other components, which are not shown in FIG. 1, such as a beam expander, folding mirrors, focusing lenses, cylindrical lenses, beam splitters, etc.

The illumination subsystem may also include deflector 14. Deflector 14 may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed.

As shown in FIG. 1, the illumination subsystem may be configured to direct the beam of light to the specimen at an oblique angle of incidence. Alternatively, the illumination subsystem may be configured to direct the beam of light to the specimen at a normal angle of incidence. In such an embodiment, the illumination subsystem may not include the deflector since the normal incidence beam of light may be scanned over the specimen by relative motion of the optics with respect to the specimen and/or by relative motion of the specimen with respect to the optics. This system may also be configured to direct multiple beams of light to the specimen such as an oblique incidence beam of light and a normal incidence beam of light. The multiple beams of light may be directed to the specimen substantially simultaneously or sequentially.

The system may include a single collection channel. For example, light scattered from the specimen may be collected by lens 16, which may be a lens or a compound lens. Lens 16 may include any appropriate lens known in the art. Alternatively, lens 16 may be replaced by a reflective or partially reflective optical component such as a mirror. In addition, although one particular collection angle is illustrated in FIG. 1, it is to be understood that the collection channel may be arranged at any appropriate collection angle. The collection angle may vary depending upon, for example, the angle of incidence and/or topographical characteristics of the specimen.

The inspection system also includes multiple channels configured to detect different portions of light scattered from the specimen, which have different wavelength bands. Since the multiple channels detect light collected by a single collection channel, the multiple channels are arranged at the same collection angle. However, it is to be understood that multiple detection channels may be coupled to different collection channels. In addition, each collection channel may be positioned at a different collection angle. As such, the multiple channels may be arranged at different collection angles. Furthermore, the multiple channels may be configured to detect different portions of light scattered from the specimen substantially simultaneously. However, it is also possible that the multiple channels may be used to detect different portions of light scattered from the specimen sequentially.

In one configuration, beamsplitter 18 is configured to direct a first portion of the light collected by lens 16 to a first channel that includes detector 20. The first channel is configured to detect light scattered from the specimen having a range of wavelengths that includes the one or more incident wavelengths. In this manner, the first channel may be configured to detect scattered light in a wavelength band selected such that the detected light does not include light fluoresced from the specimen. Detector 20 may include any detector known in the art. However, detector 20 may be selected based on the one or more incident wavelengths and/or the configuration of the illumination subsystem. For example, if the amount of light available for inspection is relatively low, an efficiency enhancing detector such as a time delay integration (TDI) camera may increase the signal-to-noise ratio and throughput of the system. Other detectors such as charge-coupled device (CCD) cameras and photo-multiplier tubes (PMTs), however, may also be used as detectors in the system depending on the amount of light available for inspection and the type of inspection being performed.

As described above, the first channel is configured to detect scattered light having a wavelength range selected such that light fluoresced from the specimen is not detected. In other words, the first channel may detect light having a range of wavelengths that includes the one or more incident wavelengths or another selected wavelength range. The range of wavelengths may include a relatively narrow band of wavelengths around or near the incident wavelength(s). For example, in one embodiment, the range of wavelengths detected by the first channel may include wavelengths within about 1 nm to about 10 nm of the one or more incident wavelengths (e.g., a 10 nm wavelength band around the one or more incident wavelengths). Therefore, in a particular example, if the incident wavelength is about 355 nm, the range of wavelengths of the first portion of light detected by the first channel may include wavelengths from about 350 nm to about 360 nm. Alternatively, for an incident wavelength of about 355 nm, the first portion of the light detected by the first channel may include only light having a wavelength of about 355 nm. The range of wavelengths detected by the first channel may vary, however, depending on the wavelength(s) of light fluoresced from the specimen. Since the first channel does not detect scattered light having wavelengths outside of the narrow wavelength band around the one or more incident wavelengths, the signal-to-noise ratio of the first channel is increased.

There are several configurations that would allow the first channel of the system to detect only light having such a range of wavelengths. In one configuration, beamsplitter 18 may be configured to direct only light having a relatively narrow wavelength band around or near the incident wavelength(s) to the first channel while allowing light having other wavelengths to pass through the beamsplitter, for example, to another detection channel.

In a different configuration, the first channel may include one or more spectral filters coupled to detector 20. For example, as shown in FIG. 1, the first channel may include spectral filter 22 coupled to detector 20. The spectral filter may be configured to allow only light having a relatively narrow wavelength band around or near the incident wavelength(s) to impinge upon detector 20. In one such embodiment, the spectral filter may be a bandpass filter. In other embodiments, the spectral filter may be an edge filter or a notch filter.

In a further configuration, the first channel may include more than one spectral filter. In this manner, if the incident wavelength(s) are changed (as might be the case when specimens having substantially different characteristics are inspected), the spectral filter might be swapped out so that the first channel detects light having the different incident wavelength(s). In addition, the spectral filter might be swapped out so that the first channel can detect light having a different selected wavelength range. In addition, the spectral filter(s) may be moveable such that a particular detector may be configured either to accept only a specific range of wavelengths or to accept all scattered wavelengths by inserting or removing a filter or a set of filters into the optical path of the detection channel.

In another configuration, detector 20 may be selected and/or configured to be sensitive to only light having a relatively narrow wavelength band around or near the incident wavelength(s). In this embodiment, the first channel may not include spectral filter 22.

Beamsplitter 18 is also configured to direct a second portion of the light collected by lens 16 to a second channel that includes detector 24. The second channel is configured to detect light scattered from the specimen having a range of wavelengths that is longer than the one or more incident wavelengths. In this manner, the wavelength range of the second channel is selected to detect light that is, for example, fluoresced from the specimen. The range of wavelengths that are detected by the second channel may be separate and distinct from the range of wavelengths that are detected by the first channel. For example, the shortest wavelength detected by the second channel may be separated from the wavelengths detected by the first channel by about 5 nm or more. Therefore, if the incident wavelength is about 355 nm, the shortest wavelength in the range detected by the second channel may be about 360 nm. In this manner, the second channel may also be configured such that the detector of the second channel does not detect light having wavelengths equal to or near the one or more incident wavelengths. Therefore, the signal-to-noise ratio of the signals produced by detector 24 may be increased. Alternatively, the selected wavelength range of the second channel may be approximately the same as the selected wavelength range of the first channel.

In some embodiments, the range of wavelengths detected by the second channel may be substantially broader than the range of wavelengths detected by the first channel. For example, the first channel may be configured to detect only scattered light having wavelengths within a relatively narrow wavelength band around the incident wavelength (e.g., within about 1 nm to about 10 nm of the incident wavelength(s)). However, the second channel may detect scattered light in a wavelength range spanning about 10 nm, about 100 nm, or even about 200 nm or more.

In one embodiment, the beamsplitter may be configured to direct only light having wavelengths longer than the incident wavelength(s) to the second channel while directing light having wavelengths equal to or near the one or more incident wavelengths to the first channel as described above. In a different configuration, the second channel may include one or more spectral filters coupled to detector 24. For example, as shown in FIG. 1, the second channel may include spectral filter 26 coupled to detector 24. The spectral filter may be configured to allow only light having wavelengths longer than the incident wavelength(s) to impinge upon detector 24. In one such embodiment, the spectral filter may be an edge filter. Alternatively, the spectral filter may be a bandpass filter or notch filter. In a further configuration, the second channel may include one or more spectral filters.

The one or more spectral filters may be selected based on one or more materials of the specimen. For example, the wavelength of the fluorescent light emitted from a specimen depends on the materials that are present on the specimen and the wavelength of illumination. Therefore, when specimens having materials that fluoresce different wavelengths of light are inspected, different spectral filters may be selected. In this manner, the spectral filter placed in the optical path of the second channel may be selected so that the second channel detects light having the wavelength(s) of the fluorescence emission emitted by the particular material(s) on the specimen. In addition, as described above, the spectral filters may be moveable such that a particular detector may be configured either to accept only a specific range of wavelengths or to accept all scattered wavelengths. In another configuration, detector 24 may be selected and/or configured to be sensitive to light having wavelengths longer than the incident wavelength(s) but not to light having wavelengths around or near the incident wavelength(s). In this embodiment, the second channel may not include spectral filter 26.

Detector 24 may include any of the detectors described above. An appropriate detector may also be selected as described above. In addition, the first and second channels may include different types of detectors. For example, in one embodiment, detector 20 may be a TDI sensor, and detector 24 may be a PMT or a CCD camera. Alternatively, the first and second channels may include the same type of detectors. For example, detector 20 and detector 24 may both be TDI sensors.

As can be seen from the above description, the two detection channels may detect light scattered from the specimen in different wavelength ranges substantially simultaneously. However, it may also be desirable in some applications, to detect light scattered from a specimen in only one wavelength range. In other words, it may be desirable to detect light scattered from a specimen with fewer than all available detection channels in an inspection system. Alternatively, multiple detection channels may be configured to detect light scattered in the same wavelength range. For instance, it may be desirable to detect only light fluoresced from a specimen in some applications.

Alternatively, it may be desirable to detect only light scattered from the specimen at approximately the one or more incident wavelengths. In other words, the wavelength range of the detected light may be selected such that light fluoresced from the specimen is not detected. The systems described herein provide substantial flexibility in the type and number of detection channels that are used to detect scattered light from a specimen. Therefore, the systems described herein also provide substantial flexibility in the wavelength range(s) of the light scattered from a specimen that are detected.

The system shown in FIG. 1 also includes processor 28. Processor 28 is configured to receive signals from detectors 20 and 24. In one embodiment, the processor may be coupled directly to the detectors by a transmission medium as shown by the dotted lines in FIG. 1. Alternatively, the processor may receive signals from electronic components (not shown) coupled to detectors 20 and 24. In this manner, the processor may be indirectly coupled to the detectors by a transmission medium and the electronic components.

The processor is configured to detect features, defects, or light scattering properties of the specimen using signals from the first and second channels. The signals produced by the first and second channels are representative of the light detected by the first and second channels. Therefore, the processor uses information about both the light scattered from the specimen at about the incident wavelength(s) and the light fluoresced from the specimen at wavelengths longer than the incident wavelength(s) to detect features, defects, or light scattering properties of the specimen.

Alternatively, the processor may be configured to detect features, defects, or light scattering properties of the specimen using signals from fewer than all of the detection channels in the inspection system. For instance, in some embodiments, the processor may use signals representative of light fluoresced from the specimen to detect defects on the specimen but not signals representative of light scattered from the specimen at approximately the one or more incident wavelengths (or vice versa). The signals that are used by the processor for defect detection may vary depending upon, for example, the characteristics of the specimen and/or the defects of interest. The processor may include any appropriate processor known in the art. In addition, the processor may be configured to use any appropriate defect detection algorithm or method known in the art. For example, the processor may use a die-to-database comparison or a thresholding algorithm to detect defects on the specimen.

As such, the inspection system provides more features, defects, or light scattering property information about specimens than other inspection systems that detect light scattered at wavelengths across the full available wavelength range of both features of interest and background features. In addition, the inspection system is configured to detect both light scattered at or near the incident wavelength(s) and fluorescent light scattered from the specimen substantially simultaneously. Therefore, the inspection system provides a substantial amount of information about specimens being inspected in a relatively short amount of time.

The processor may also be configured to determine one or more film properties of the specimen using signals from the first and/or second channels. The processor may be configured to determine the one or more film properties using the signals and any appropriate algorithm or method known in the art. Therefore, the system may determine information not only about defects on the specimen but also information about other structures or films on the specimen as well. Since the signals that are used for defect detection and film property determination can be generated substantially simultaneously, the systems and methods described herein provide more information than other inspection systems and methods without decreasing the throughput.

In addition, the information provided by the inspection system may advantageously be used to classify features or defects detected on a specimen. For example, an intensity of the first detected portion of light, an intensity of the second detected portion of light, or a combination thereof may be used to classify features or defects detected on a specimen. In one particular example, many types of organic materials (e.g., photoresist particles) with a significant contribution of longer wavelength fluorescence in their scattering spectrum could be discriminated from inorganic material (e.g., metal particles) with no or relatively low contributions of fluorescence in their scattering spectrum. Therefore, defects may be classified by comparing the intensity of the different detected portions of light or by the intensity of a particular portion of scattered light.

Although the system illustrated in FIG. 1 is shown to include only two detection channels, it is to be understood that the system may include more or less than two detection channels. For example, the system may include only the first or the second channel. In addition, the system may include a third channel. In one embodiment, the third channel may be configured to detect light scattered from the specimen having a range of wavelengths shorter than the one or more incident wavelengths. For example, there may be unusual mechanisms (e.g., non-linear optical effects) that are important or that may change the spectrum of light scattered from a specimen. Examples of such unusual mechanisms may include frequency up-conversion or frequency doubling, which may result in scattered light having a wavelength that is approximately one half that of the incident wavelength.

Alternatively, the third channel may be configured to detect light scattered from the specimen having a range of wavelengths longer than the one or more incident wavelengths but different than the wavelength range detected by the second channel. In this manner, the second and third channels may both detect light fluoresced from the specimen. However, the second and third channels may detect different wavelengths of fluoresced light, which may be emitted by different materials on the specimen. In some embodiments, the range of wavelengths detected by the third channel may be substantially broader than the range of wavelengths detected by the first channel. For example, the third channel may detect scattered light in a wavelength range spanning about 10 nm, about 100 nm, or about 200 nm or more.

One example of an inspection system that includes more than two channels for detecting light scattered from a specimen in different wavelength bands is illustrated in FIG. 2. This inspection system includes an illumination subsystem, which may be configured as described above. For example, the illumination subsystem includes light source 10 and deflector 14, which may be configured as described above. The illumination subsystem, light source 10, and deflector 14 may be further configured as described above.

In addition, the system includes lens 16, which may be configured as described above. Lens 16 collects light scattered from specimen 12. The collected light may be directed to three different channels. For example, the collected light may be directed to a first channel that includes detector 30, a second channel that includes detector 32, and a third channel that includes detector 34. Therefore, each of the three channels may detect different portions of light scattered from the specimen substantially simultaneously. The different portions of light may have different wavelength bands. The collected light may be directed to the three different channels by beamsplitters 36 and 38 or other suitable optical components. The beamsplitters may be configured as described above.

In addition, spectral filters 40, 42, and 44 may be coupled to detectors 30, 32, and 34, respectively. Although only one spectral filter is shown coupled to each detector, it is to be understood that more than one spectral filter may be coupled to each detector. In addition, although a spectral filter is shown coupled to each detector, it is to be understood that spectral filters may be coupled to only some of the detectors. The configuration of the spectral filters may be determined as described above based on the wavelengths of the scattered light that are to be detected by the detectors. Alternatively, as described further above, the three channels may not include any spectral filters.

The first channel is configured to detect scattered light having a range of wavelengths that includes the one or more incident wavelengths. In particular, the first channel may be configured to detect a relatively narrow band of wavelengths around or near the one or more incident wavelengths. In this manner, the first channel may not detect fluorescent light scattered from the specimen. Such a range of wavelengths is described in more detail above. The second channel is configured to detect scattered light having wavelengths that are longer than at least one of the one or more incident wavelengths. As such, the second channel may detect light fluoresced from the specimen. The third channel may be configured to detect scattered light having wavelengths that are shorter than the one or more incident wavelengths. Therefore, the third channel may detect light scattered from the specimen due to non-linear optical effects, for example. Alternatively, the third channel may be configured to detect scattered light having wavelengths that are longer than at least one of the one or more incident wavelengths and that are different than the wavelength band detected by the second channel. In this manner, the third channel may detect light fluoresced from one material on the specimen, and the second channel may detect light fluoresced from another material on the specimen.

The system illustrated in FIG. 2 may also include processor 28, which may be configured to receive signals from the first, second, and/or third channels or from electronic components (not shown) coupled to the detectors of the first, second, and/or third channels. The signals generated by the first, second, and third channels are representative of the different portions of light detected by each channel. In addition, the processor may be configured to detect defects and/or features of interest on the specimen using the signals from the first, second, and/or third channels. The processor may also be configured to determine one or more properties of films or light scattering properties of the specimen using signals from the first, second, and/or third channels. Furthermore, the processor may be configured to classify defects on the specimen using the signals from the first, second, and/or third channels. The processor may detect defects or features of interest, determine properties of films, and/or classify defects on the specimen as described above. The system shown in FIG. 2 may be further configured as described above.

One example of another inspection system that can be used to perform a method for inspecting a specimen as described herein is illustrated in FIG. 3. The inspection system shown in FIG. 3 is an inspection tool configured for patterned and/or unpatterned wafer inspection and is based on the SP1$^{TBI}$ system, which is commercially available from KLA-Tencor, San Jose, Calif. A similar inspection system is described in U.S. Pat. No. 6,538,730 to Vaez-Iravani et al., which is incorporated by reference as if fully set forth herein. It is to be understood that the system illustrated in FIG. 3 may be further configured as described in this patent. In addition, U.S. Pat. No. 6,538,730 is related to U.S. Pat. Nos. 6,201,601 to Vaez-Iravani et al. and 6,271,916 to Marxer et al., which are also incorporated by reference as if fully set forth herein. The inspection system described herein may be further configured as described in these patents.

Specimen 46 to be inspected is illuminated by normal incidence beam 48 and/or oblique incidence beam 50, which may be generated by light sources 52 and 54, respectively. The light sources may include any suitable light sources described above. Light sources 52 and 54 form an illumination subsystem that is configured to direct light having one or more incident wavelengths to a specimen. In this system, the one or more incident wavelengths of one or both of the light sources may be selected to stimulate fluorescence emission from one or more materials on the specimen. For example, the wavelength(s) of light source 52 may be selected to stimulate fluorescence from a first material on the specimen, and the wavelength(s) of light source 54 may be selected to stimulate fluorescence from a second material on the specimen.

In one embodiment, both light sources 52 and 54 may be configured to emit ultraviolet light or visible light. Alternatively, one of the light sources may be configured to emit ultraviolet light, and the other light source may be configured to emit visible light. The light sources may emit monochromatic or near monochromatic light. Alternatively, the light sources may emit broadband light. In such an embodiment, spectral filters such as bandpass filters may be coupled to the light sources such that light in a relatively narrow wavelength band is directed to the specimen.

The system may also include a number of optical components such as folding mirrors (that are not shown in FIG. 3 for simplicity) to direct the beams to the surface of the specimen as shown in FIG. 3. Specimen 46 is supported on a chuck (not shown), which may be rotated and translated such that beams 48 and/or 50 illuminate an area or spot on the specimen which is caused to move in a spiral path on the surface of the specimen. Alternatively, beams 48 and/or 50 may be caused to move in a manner known to those skilled in the art to trace the spiral path or another type of scan path across the specimen.

The area or spot illuminated by either one or both of the beams on the specimen scatters light from the beam(s). The light scattered by the illuminated area on the specimen along directions close to perpendicular to the surface of the specimen is collected and focused by lens collector 56 and directed by mirror 58 and beamsplitter 60 to detectors 62 and 64. Since lens collector 56 collects light scattered along directions close to the normal direction, this collection channel is referred to as the narrow channel. Detectors 62 and 64 together may form a first detection channel. The first detection channel may be configured to detect light scattered from the specimen having a range of wavelengths that includes the one or more incident wavelengths. In this manner, a wavelength range of the first detection channel may be selected such that light fluoresced from the specimen is not detected. Such a range of wavelengths may include wavelength ranges described above. In such an embodiment, one of the detectors may be used for unpatterned wafer inspection, and the other detector may be used for patterned wafer inspection as described further below. Alternatively, detector 62 may be part of a first detection channel, and detector 64 may be part of a second detection channel (or vice versa). In such an embodiment, detectors 62 and 64 are coupled to the same lens collector (lens 56). Therefore, the first and second channels may be arranged at the same collection angle. In addition, detectors 62 and 64 may be of the same type or may be of different types.

In addition, spectral filters 66 and 68 may be coupled to detectors 62 and 64, respectively. Furthermore, more than one spectral filter may be coupled to each detector. Alternatively, spectral filters may be coupled to only one or none of the detectors. The spectral filters may be configured and selected as described above. When desired, one or more polarizers (not shown) may be placed in the path of the collected light in one or both of the detection channels.

Light scattered by the spot on the specimen illuminated by either one or both of the beams along directions away from the normal direction is collected by ellipsoidal mirror 70 and may be focused through an aperture (not shown) and optional polarizers (not shown) to detector 72. In addition, beamsplitter 74 is configured to direct a portion of the light collected by ellipsoidal mirror 70 to detector 76. Since the ellipsoidal mirror collects scattered light along directions at wider angles from the normal direction than lens collector 56, this collection channel is referred to as the wide channel. Detectors 72 and 76 together may form a second detection channel. The second channel may be configured to detect light scattered from the specimen having a range of wavelengths longer than the one or more incident wavelengths (i.e., fluorescent light scattered from the specimen).

In an alternative embodiment, the second channel may be configured to detect light scattered from the specimen having a range of wavelengths that is shorter than the one or more incident wavelengths (i.e., light scattered from the specimen and due to non-linear optical effects). In such an embodiment, one of the detectors may be used for unpatterned wafer inspection, and the other detector may be used for patterned wafer inspection as described further below. Alternatively, detector 72 may be part of the first detection channel, and detector 76 may be part of the second detection channel (or vice versa). Since detectors 72 and 76 are coupled to the same collector (mirror 70), the first and second channels may be arranged at the same collection angles. In such an embodiment, detectors 72 and 76 may be of the same type or may be of different types.

In addition, spectral filters 78 and 80 may be coupled to detectors 72 and 76, respectively. Furthermore, more than one spectral filter may be coupled to each detector. Alternatively, spectral filters may be coupled to only one or none of the detectors. The spectral filters may be configured and selected as described above.

The first and second channels may also be arranged at different collection angles. For example, detectors 62 and/or 64 may form the first channel, and detectors 72 and/or 76 may form the second channel. Since detectors 62 and 64 are coupled to lens 56, and detectors 72 and 76 are coupled to mirror 70, detectors 62 and 64 are arranged at a collection angle that is different than the collection angle of detectors 72 and 76.

The optical configuration of the system shown in FIG. 3, therefore, obviously provides a great deal of flexibility in the illumination subsystem, collection channels, and detection channels. The particular configuration of the system that is employed may vary depending on the characteristics of the specimen being inspected and/or the type of information about the specimen that is to be obtained. In addition, there are many other variations that the system configuration may have that are not shown in FIG. 3. For example, the system may include less than 4 detectors. Alternatively, the system may include more than 4 detectors. Light from one of the collectors shown in FIG. 3 may be directed to additional detectors by additional beamsplitters or other optical components. Even though such a configuration is not shown in FIG. 3, it will be obvious to one of ordinary skill in the art how such a configuration could be implemented. In addition, the system may include additional optical components (not shown) such as polarizers, masks, other filters, or any other suitable optical component known in the art.

The system shown in FIG. 3 may also include more than two detection channels. For example, one of the detectors shown in FIG. 3 may form a third detection channel. The third channel may be configured as described above. Alternatively, the system shown in FIG. 3 may include additional detectors (not shown) that form a third channel. The additional detectors may be coupled to lens 56 and/or mirror 70. Alternatively, the additional detectors may be coupled to an additional collector (not shown).

Outputs of detectors 62, 64, 72, and 76 are supplied to processor 82. For example, detectors 62, 64, 72, and 76 may be coupled to processor 82 by a transmission medium as shown by the dotted lines in FIG. 3. Processor 82 may process the signals from the first and second channels as described above and may determine the presence of features and/or defects and their characteristics. In addition, processor 82 may be configured to classify defects detected on the specimen as described above. Furthermore, processor 82 may be configured to determine one or more film properties or light scattering properties of the specimen as described above.

The following describes a configuration of the system shown in FIG. 3 that is suitable for inspection of unpatterned and patterned wafers. The collection optics of the system shown in FIG. 3 are rotationally symmetric about the normal direction. The lens collector and the ellipsoidal mirror preserve the azimuthal and polar information contained in light scattered by defects on the surface of the specimen. Therefore, certain defects and/or patterns on the specimen may scatter light preferentially along certain azimuthal and polar directions more than other azimuthal and polar directions. By making use of the preserved azimuthal and polar information in the light collected by lens 56 and mirror 70, the system is advantageously adapted and modified for the detection of defects on patterned wafers. In addition, the system is advantageously modified for detection of defects in the edge portion of patterned and unpatterned wafers.

By segmenting a portion of the light collected by the lens and/or the ellipsoidal mirror, light scattered in different azimuthal and polar directions may be detected separately. In this manner, some segments of the detectors detecting light diffracted or scattered by a pattern may become saturated, while other segments of the detectors will yield useful signals for the detection and classification of defects on the specimen. Since the lens and the ellipsoidal mirror preserve the azimuthal and polar information of the scattered light, knowledge of the type of pattern, features, or defects present on the specimen can be advantageously used to design and position multiple detectors to advantageously detect and classify the defects on the specimen. This is especially true in the case of regular patterns such as memory structures on the specimen since light diffracted by regular patterns also tends to be regular.

A convergent hollow cone of light may be collected by lens 56 and/or mirror 70. In the case of lens 56, a spatial filter (not shown) may be employed to block the specular reflection of the normal incidence beam from reaching detectors 62 and 64 so that the light focused by lens 56 to detectors 62 and 64 has the shape of a convergent hollow cone. In the case of the ellipsoidal mirror, since the mirror is not a complete ellipse, it collects only light scattered at larger angles to the normal direction without also collecting the light scattered at near normal directions so that the light focused by mirror 70 towards detectors 72 and 76 also has the shape of a convergent hollow cone.

An arrangement of multiple fiber channels (not shown) receiving light in the convergent cone of light such as that collected by mirror 70 may be used to direct light to one of the two detectors configured to detect light collected by the mirror (e.g., detector 76). One arrangement includes two substantially concentric rings of optical fiber channels (not shown) that are used to carry the collected scattered light in the convergent hollow cone. Another arrangement of the multiple fiber channels may include one ring of optical fiber channels (not shown) that can be used to carry the collected scattered light. Fourier components or other scattering from features on the specimen may reach some of the fibers thereby causing the detectors detecting the light from such channels to be saturated. However, there will be other optical fiber channels that do not receive such unwanted pattern or feature scattering. The use of multiple fiber channels effectively segments the collected scattered light into different sectors or segments so that only some of the fiber channels will receive a strong signal and can become saturated due to Fourier or other feature scatter leaving the remaining channels carrying information that can be analyzed for detecting anomalies. Since the azimuthal and polar information in the collected scattered light is preserved, various schemes may be used to minimize the effects of the pattern or feature scatter when the segmented approach is used.

In a similar manner, the fiber channels may be used to segment the collected scattered light into portions having different wavelength ranges. The different segments may then be directed to different detection channels that are suitable for detection of specific wavelength ranges. Signals produced by the detection channels may be selectively used for analysis of a specimen based on, for example, one or more characteristics of a specimen or defects of interest on the specimen.

Different types of segmented detectors may be used to detect the light carried by the fiber channels such as a multi-anode photo-multiplier tube (PMT) or a multi-PIN diode array. In the event that a multi-anode PMT is used, however, there may be a nominal 3% cross-talk between any two adjacent channels. To avoid such cross-talk, the fibers may be aligned with every other PMT anode. This arrangement avoids the 3% cross-talk that may be present if all of the anodes are aligned with fibers. In addition, the optically transmissive cores of optical fibers that are located adjacent to each other may be separated from each other by the claddings that envelope the cores so that cross-talk between adjacent cores may be reduced. Obviously, optical channels other than fibers may be used and are within the scope of this disclosure. Where such channels do not include separators such as the claddings in the case of optical fibers, other optical separators may be used to reduce cross-talk.

As described above, beamsplitter 60 reflects and diverts a portion of the collected light from lens 56 to an arrangement of optical fibers (not shown). Preferably, the size of the optical fibers collect and convey most of the light in the hollow cone of light. Each of the fibers may be connected to a corresponding detector or a detecting unit in a multi-unit or multi-element detector. In a similar manner, beamsplitter 74 diverts a portion of the light collected by mirror 70 towards an arrangement of optical fiber channels (not shown) where each channel is connected to a separate detector or separate detecting unit in a multi-element detecting system. As shown in FIG. 3, beamsplitter 74 is configured such that it diverts light only within a narrow ring to the arrangement of optical fiber channels. Most of the light collected by mirror 70 is passed through beamsplitter 74 and focused to detector 72 to provide a single output. Therefore, the system illustrated in FIG. 3 diverts a portion of the scattered light collected by lens 56 and mirror 70 and directs this portion of the scattered light towards fibers to convey the segmented light to segmented detectors 64 and 76. In this manner, a single instrument may include different types of detection channels coupled to each collection channel; one non-segmented detection channel, which is particularly suitable for unpatterned specimen inspection, and one segmented detection channel, which is particularly suitable for patterned specimen inspection. It is also possible to place the individual detectors or multi-element detecting systems directly in the path of the converging hollow cone of light, rather than in the path of individual optical fibers.

Where the system illustrated in FIG. 3 is used for inspecting specimens with memory cells formed thereon, the Fourier components from the memory array will spin as the specimen is rotated. These components will thus rotate and be at different azimuthal angles about the normal direction. As a result, these Fourier components will be conveyed by different fibers as the specimen is rotated. Since the array of memory cells may have different dimensions in the X and Y directions of the specimen, as the specimen rotates, the number of detectors that are saturated by the Fourier components will change. By knowing the X and Y dimensions of the memory cells, the number of Fourier diffraction components can be estimated.

Alternatively, during an initialization process at the beginning, a learn cycle may be performed where the maximum number of Fourier components that need to be eliminated is determined by noting the maximum number of detectors with very strong, or saturated, outputs. During the subsequent measurement, this number of detector outputs may then be eliminated, where the outputs eliminated are the ones that are saturated or the ones that have the largest values. In the case of a multi-anode PMT, for example, where each anode is used and is connected to a corresponding fiber, cross-talk may be reduced by also eliminating the components adjacent to the detectors having the highest outputs. For example, if the specimen in one position gives three Fourier components, and in another two, the three direct components together with the two components adjacent to each would be eliminated for a total of nine detector outputs that are eliminated. This leaves seven usable detector outputs. This number will be maintained regardless of the exact orientation of the specimen. This allows the user to maintain the sizing option for the particles.

Preferably, the fibers or the segmented detectors are arranged rotationally symmetrically around a direction. When arranged in such manner, the light scattering directions are partitioned into identical angular segments and light scattered within each segment is collected by a corresponding fiber. When mirror 58 and beamsplitters 60 and 74 reflect or divert a portion of the light collected by lens 56 or mirror 70, the azimuthal and polar positions of the collected scattered light are preserved when the reflected or diverted light is directed to the fibers or the segmented detectors. Therefore, azimuthal and polar characterizations of scattered light are preserved both for the narrow and the wide channels.

If all of the scattered light from the illuminated spot on the specimen is collected and directed to a single non-segmented detector, the presence of Fourier or other scatter components will cause the detector to saturate so that the system will not be able to provide useful information concerning anomalies in the illuminated spot. For this reason, the collected scattered light is segmented into different segments. If the collected scattered light is divided into very few segments, such as two or three, resulting in two or three output signals, the probability may be high that the two or three segments would still contain pattern scatter so that the two or three detectors would again become saturated and yield no useful information concerning detects. Thus to be useful, the segmentation is preferably fine enough that at least some of the detector signals contain no significant pattern scatter. For example, as explained in more detail in U.S. Pat. No. 6,538,730 to Vaez-Iravani et al., where the segmented light is conveyed to multiple optical fibers, it is preferable for at least some of the fibers to receive light collected within azimuthal angles of no more than δφ.

The system illustrated in FIG. 3 is particularly advantageous for distinguishing between micro-scratches and particles as further described in U.S. Pat. No. 6,538,730 to Vaez-Iravani et al. The system illustrated in FIG. 3 may be further configured as described in this patent.

Figure 4:
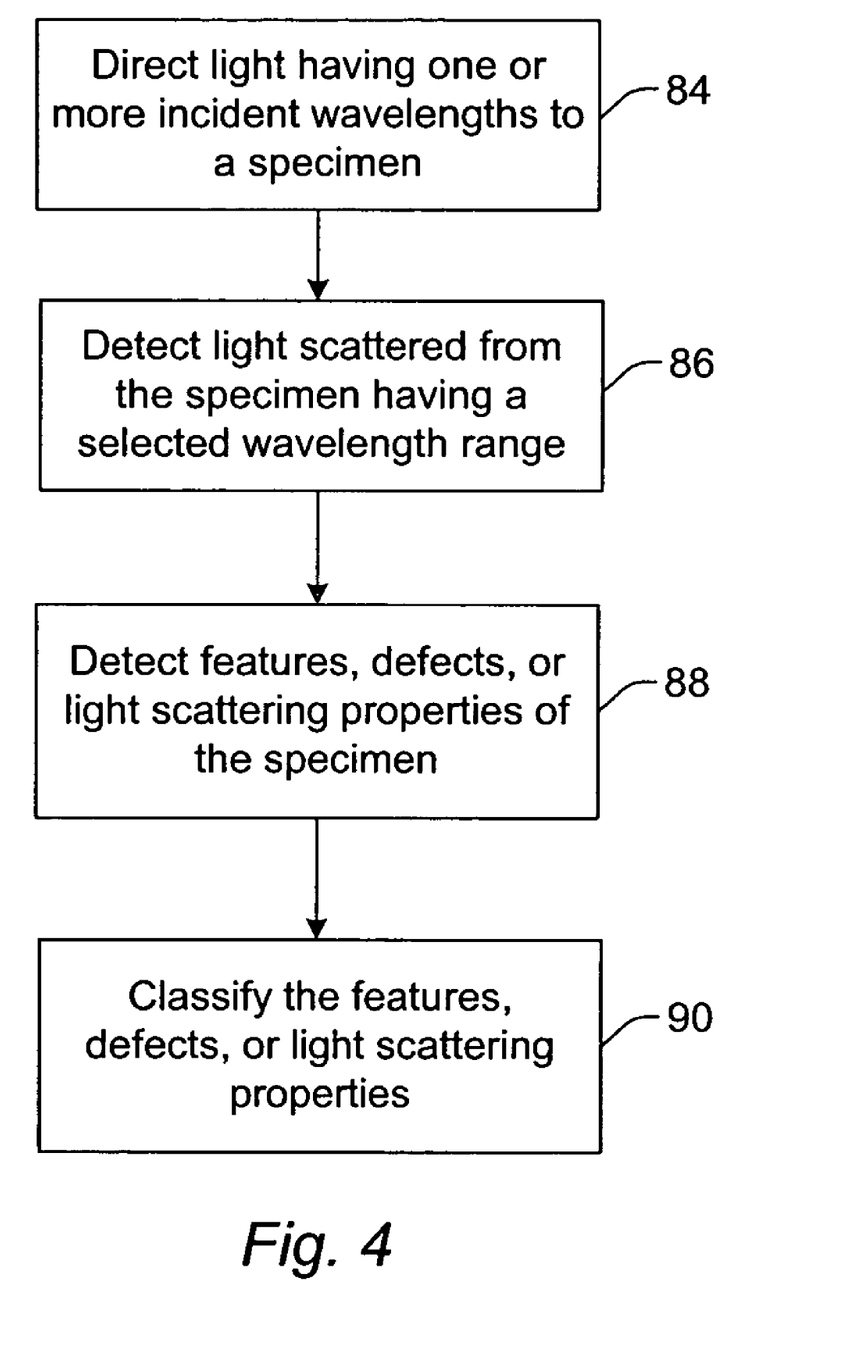
FIG. 4 is a flow chart illustrating an embodiment of a method for inspecting a specimen.

FIG. 4 illustrates an embodiment of a method for inspecting a specimen. The method may be performed using any of the inspection systems described above. The method includes directing light having one or more incident wavelengths to the specimen, as shown in step 84. In one embodiment, the one or more incident wavelengths may be selected to stimulate fluorescence emission from one or more materials on the specimen. In some embodiments, the one or more incident wavelengths are ultraviolet wavelengths such that the light directed to the specimen is ultraviolet light. In one such embodiment, the ultraviolet light may be nearly monochromatic ultraviolet light. The method also includes detecting light scattered from the specimen that has a selected wavelength range, as shown in step 86. In another embodiment, directing light to the specimen and detecting light scattered from the specimen may be performed in a non-confocal mode and/or a darkfield mode.

The selected wavelength range may include wavelengths within about 1 nm to about 10 nm of the one or more incident wavelengths. In this manner, a wavelength range of the detected light is selected such that light fluoresced from the specimen is not detected. Alternatively, the detected light may include light fluoresced from the specimen. In some embodiments, the selected wavelength range may include wavelengths shorter than at least one of the one or more incident wavelengths. In a different embodiment, the method may include detecting light scattered from the specimen having a different selected wavelength range. In some embodiments, the method may include separately detecting different portions of light substantially simultaneously that have different wavelength ranges. In one such embodiment, one wavelength range may be selected to not include light fluoresced from the specimen, and another wavelength range may be selected to include light fluoresced from the specimen.

In addition, the method includes detecting features, defects, or light scattering properties of the specimen using signals representative of the detected light, as shown in step 88. In some embodiments, the method may further include classifying the features, the defects, or the light scattering properties using an intensity of one or more of the different portions of the detected light, as shown in step 90. The method may include additional steps described herein.

Each of the systems described herein may not be coupled to other tools except by one or more transmission mediums. A transmission medium may include "wired" and "wireless" portions. In this manner, the systems described herein may be configured as stand-alone tools. Alternatively, the systems may be incorporated into another tool such as a process tool (not shown). In this manner, the system may be configured to detect features, defects, and/or light scattering properties of a specimen during a process carried out in the process tool.

Alternatively, or in addition, the system may be configured to detect features, defects and/or light scattering properties of a specimen while the specimen is disposed within the process tool but before or after a process carried out in the process tool. In some embodiments, the system may be coupled to the process tool by a common stage, a common specimen handler, a common power source, and/or a common processor. The process tool may include a cluster tool that may be used to fabricate semiconductor devices or a tool that is used to fabricate or inspect reticles. Examples of process tools that the system may be coupled to include, but are not limited to, a lithography tool, an etch tool, a chemical-mechanical polishing tool, a deposition tool, a plating tool, and a cleaning tool.

In an embodiment, the methods described herein may include altering a parameter of a process tool in response to features, defects and/or light scattering properties detected on the specimen using a feedback control technique or a feedforward control technique. The process tool may be, for example, a lithography tool, a chemical-mechanical polishing tool, an etch tool, or a cleaning tool used to process the specimen. For example, defects on a wafer after a cleaning process may adversely affect the properties of semiconductor devices formed on the wafer. Therefore, parameters of a cleaning tool may be altered in response to defects detected on a wafer processed in the cleaning tool using a feedback control technique to alter the cleaning process. In this manner, a parameter of a process tool may be altered for processing additional specimens. Preferably, the parameters of the process tool may be altered such that the additional specimens have fewer defects than the inspected specimen.

The process tool may also include a process tool used for further processing of the inspected specimen. For example, such a process tool may be a deposition tool, a plating tool, or a cleaning tool. In this manner, a parameter of a process tool may be altered for further processing of the inspected specimen. In a further embodiment, a processor as described herein may be coupled to the process tool and may be configured to alter a parameter of the process tool in response to the detected defects using a feedback control technique or a feedforward control technique.

The following example is presented merely to illustrate aspects and advantages of the systems and methods described herein and is not intended as limitations of this invention.

Example

Effect of Fluorescence Filter on Detection Sensitivity with Ultraviolet Illumination Various wafers with different types of materials formed thereon as unpatterned films were inspected using ultraviolet illumination and visible illumination. The inspection systems used to perform the different inspections were similarly configured other than the illumination type. The ultraviolet illumination had a wavelength of 355 nm and a power of 350 mW. The visible illumination has a wavelength of 488 nm and a power of 75 mW. As can be seen from Table 1, the ultraviolet illumination provided increased sensitivity for some material types in comparison with visible illumination. The sensitivities are reported as nm latex sphere equivalent (LSE) thresholds using estimates from defect histograms and detectable PSL sizes. In addition, the different wafer types were also inspected using the ultraviolet illumination described above in addition to using a fluorescence filter to filter the detected light. The fluorescence filter was a 355 nm bandpass filter. As can be seen from Table 1, the use of the fluorescence filter in combination with ultraviolet illumination provided better sensitivity than that of the other inspection configurations for all of the different wafer types.

TABLE 1

| Wafer Type | Sensitivity (nm) with Visible Illumination | Sensitivity (nm) with UV Illumination | Sensitivity (nm) with UV Illumination and Fluorescence Filter |
|---|---|---|---|
| 1 | 72 | 61 | 54 |
| 2 | 72 | 59 | 54 |
| 3 | 130 | ~350 | 89 |
| 4 | 105 | ~300 | 81 |

Haze measurements were also made for each of the above different types of materials using ultraviolet illumination with and without a fluorescence filter. Haze is generally defined as surface scatter of a specimen. The results of these measurements are illustrated in Table 2.

TABLE 2

| Wafer type | Haze (ppm) with UV Illumination | Haze (ppm) with UV Illumination and Fluorescence Filter |
|---|---|---|
| 1 | 1.52 | 0.144 |
| 2 | 1.54 | 0.140 |
| 3 | 29.7 | 0.266 |
| 4 | 31.4 | 0.354 |

Further modifications and alternative embodiments of various aspects of the invention may be apparent to those skilled in the art in view of this description. For example, methods and systems for inspecting a specimen using light scattered in different wavelength ranges are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for inspecting a specimen, comprising:
   directing ultraviolet light to the specimen;
   collecting light scattered from the specimen with a collection channel;
   detecting light collected by the collection channel with multiple detection channels, wherein the detected light has a selected wavelength range, and wherein the wavelength range is selected such that light fluoresced from the specimen is not detected thereby reducing background signal representative of a surface of the specimen detected by the multiple detection channels and increasing the signal-to-noise ratio of the multiple detection channels; and
   detecting features, defects, or light scattering properties of the specimen using signals representative of the detected light.

2. The method of claim 1, wherein the ultraviolet light comprises nearly monochromatic ultraviolet light.

3. The method of claim 1, wherein the wavelength range comprises wavelengths within about 1 nm to about 10 nm of a wavelength of the ultraviolet light.

4. The method of claim 1, wherein the light detected by the multiple detection channels has different selected wavelength ranges.

5. The method of claim 1, further comprising collecting light scattered from the specimen with an additional collection channel, wherein the collection and additional collection channels are arranged at different collection angles.

6. The method of claim 1, further comprising collecting light scattered from the specimen with an additional collection channel and detecting light collected by the additional collection channel with at least one detection channel, wherein the collection and additional collection channels are arranged at different collection angles, and wherein the light detected by the multiple detection channels has the same selected wavelength range as the light detected by the at least one detection channel.

7. The method of claim 1, further comprising classifying the features or defects using the signals representative of the detected light.

8. A method for inspecting a specimen, comprising:
   directing ultraviolet light to the specimen;
   detecting light scattered from the specimen with one or more channels, wherein at least one of the one or more channels comprises two or more detectors, wherein each of the two or more detectors has an independently selected wavelength range, and wherein the wavelength range is selected such that light fluoresced from the specimen is not detected thereby reducing background signal representative of a surface of the specimen detected by the two or more detectors and increasing the signal-to-noise ratio of the two or more detectors; and
   detecting features, defects, or light scattering properties of the specimen using signals representative of the detected light.

9. The method of claim 8, further comprising classifying the features or defects using the signals representative of the detected light.

10. A method for inspecting a specimen, comprising:
    directing light having one or more incident wavelengths to the specimen;
    collecting light scattered from the specimen with a collection channel;
    separately detecting a first portion and a second portion of light collected by the collection channel substantially simultaneously with multiple detection channels, wherein the first and second portions have a wavelength range selected such that the first and second portions do not include light fluoresced from the specimen thereby reducing background signal representative of a surface of the specimen detected by the multiple detection channels and increasing the signal-to-noise ration of the multiple detection channels; and
    detecting features, defects, or light scattering properties of the specimen using signals representative of the first and second portions of the light.

11. The method of claim 10, wherein the one or more incident wavelengths are ultraviolet wavelengths.

12. The method of claim 10, wherein the wavelength range of the first portion comprises wavelengths within about 1 nm to about 10 nm of the one or more incident wavelengths.

13. The method of claim 10, further comprising classifying the features or defects using an intensity of the first portion, an intensity of the second portion, or a combination thereof.

14. The method of claim 10, wherein said directing and said separately detecting are performed in a non-confocal mode.

15. The method of claim 10, wherein said directing and said separately detecting are performed in a darkfield mode.

16. An inspection system, comprising:
   an illumination subsystem configured to direct ultraviolet light to a specimen;
   a collection channel configured to collect light scattered from the specimen;
   multiple detection channels configured to detect light collected by the collection channel having a selected wavelength range, wherein the wavelength range is selected such that light fluoresced from the specimen is not detected thereby reducing background signal representative of a surface of the specimen detected by the multiple detection channels and increasing the signal-to-noise ration of the multiple detection channels; and
   a processor configured to detect features, defects, or light scattering properties on the specimen using signals that are representative of the detected light.

17. The system of claim 16, further comprising a second collection channel, wherein the collection channel and the second collection channel are arranged at different collection angles.

18. The system of claim 17, further comprising second multiple detection channels configured to detect light collected by the second collection channel.

19. The system of claim 16, wherein the multiple detection channels comprise different types of detectors.

20. The system of claim 16, wherein the multiple detection channels comprise the same type of detectors.

21. The system of claim 16, wherein one of the multiple detection channels comprises a bandpass filter, and wherein another of the multiple detection channels comprises an edge filter, a notch filter, or a combination thereof.

22. The system of claim 16, wherein the multiple detection channels comprise one or more spectral filters, and wherein the one or more spectral filters are selected based on one or more materials of the specimen.

23. The system of claim 16, wherein the multiple detection channels are configured to detect the light having different selected wavelength ranges.

24. The system of claim 16, wherein the illumination subsystem and the multiple detection channels form a non-confocal optical subsystem.

25. The system of claim 16, wherein the illumination subsystem and the multiple detection channels form a darkfield optical subsystem.

* * * * *